(12) United States Patent
Duftner et al.

(10) Patent No.: US 9,227,064 B2
(45) Date of Patent: *Jan. 5, 2016

(54) EXTERNAL BUTTON PROCESSOR WITH A RECHARGEABLE BATTERY

(71) Applicant: MED-EL Elektromedizinische Geraete GmbH, Innsbruck (AT)

(72) Inventors: Alexander Duftner, Innsbruck (AT); Erwin S. Hochmair, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/479,402

(22) Filed: Sep. 8, 2014

(65) Prior Publication Data

US 2015/0005844 A1 Jan. 1, 2015

Related U.S. Application Data

(63) Continuation of application No. 13/632,182, filed on Oct. 1, 2012, now Pat. No. 8,831,728, which is a continuation of application No. 12/534,298, filed on Aug. 3, 2009, now Pat. No. 8,280,524.

(60) Provisional application No. 61/087,276, filed on Aug. 8, 2008.

(51) Int. Cl.
*A61N 1/37* (2006.01)
*A61N 1/36* (2006.01)
(Continued)

(52) U.S. Cl.
CPC .......... *A61N 1/36032* (2013.01); *A61N 1/3787* (2013.01); *A61N 1/37229* (2013.01); *A61N 1/375* (2013.01); *A61N 1/3758* (2013.01)

(58) Field of Classification Search
CPC ............ A61N 1/0541; A61N 1/36032; A61N 1/3787; A61N 2/02
USPC .................................. 607/55, 56, 57, 33, 155
See application file for complete search history.

(56) References Cited

U.S. PATENT DOCUMENTS 4,259,416 A 3/1981 Ikeda et al. .................... 429/94
4,352,960 A 10/1982 Dormer et al. ................ 179/107
(Continued)

FOREIGN PATENT DOCUMENTS

WO WO 01/39830 A2 6/2001 ............... A61N 1/36
WO WO 01/50816 A1 7/2001 ............. H04R 25/00
WO WO 2007/124325 A2 11/2007 ............... A61N 1/18

OTHER PUBLICATIONS

Australian Government, Patent Examination Report No. 1, pertaining to Patent Application No. 2013205893, dated Aug. 8, 2008, 3 pages.
(Continued)

*Primary Examiner* — Christopher D Koharski
*Assistant Examiner* — Natasha Patel
(74) *Attorney, Agent, or Firm* — Sunstein Kann Murphy & Timbers LLP

(57) ABSTRACT

An external processor device is described for a hearing implant system. An external processor housing has a generally planar skin contacting surface and a central axis perpendicular to the skin contacting surface. A signal processor is located within the processor housing for developing an implant data signal. The processor housing also contains a transmitter coil for coupling the implant data signal across the skin to the implantable prosthetic system. A battery container forms an annular compartment around the central axis and contains a battery arrangement to provide electrical power to the signal processor and the transmitter coil.

9 Claims, 9 Drawing Sheets

(51) Int. Cl.
*A61N 1/372* (2006.01)
*A61N 1/378* (2006.01)
*A61N 1/375* (2006.01)

(56) References Cited

U.S. PATENT DOCUMENTS

| | | | | |
|---|---|---|---|---|
| 6,067,474 | A | 5/2000 | Schulman et al. | 607/57 |
| 6,358,281 | B1 | 3/2002 | Berrang et al. | 623/10 |
| 6,380,101 | B1 | 4/2002 | Breen et al. | 438/765 |
| 7,054,691 | B1 | 5/2006 | Kuzma et al. | 607/57 |
| 2004/0133065 | A1 | 7/2004 | Easter et al. | 600/25 |
| 2005/0075693 | A1* | 4/2005 | Toy et al. | 607/60 |
| 2005/0159791 | A1 | 7/2005 | Daly et al. | 607/57 |
| 2005/0251225 | A1 | 11/2005 | Faltys et al. | 607/57 |
| 2006/0184212 | A1 | 8/2006 | Faltys et al. | 607/57 |
| 2007/0053534 | A1 | 3/2007 | Kiratzidis | 381/312 |
| 2007/0055321 | A1 | 3/2007 | Gordon et al. | 607/55 |
| 2007/0208403 | A1* | 9/2007 | Della Santina et al. | 607/137 |
| 2008/0002834 | A1 | 1/2008 | Hochmair | 381/71.2 |
| 2009/0096413 | A1* | 4/2009 | Partovi et al. | 320/108 |

OTHER PUBLICATIONS

International Searching Authority, International Search Report—International Application No. PCT/US2009/052538, dated Oct. 26, 2009, together with the Written Opinion of the International Searching Authority, 15 pages.

International Preliminary Examining Authority, International Preliminary Report on Patentability—International Application No. PCT/US2009/052538, dated Jul. 5, 2010, 9 pages.

* cited by examiner

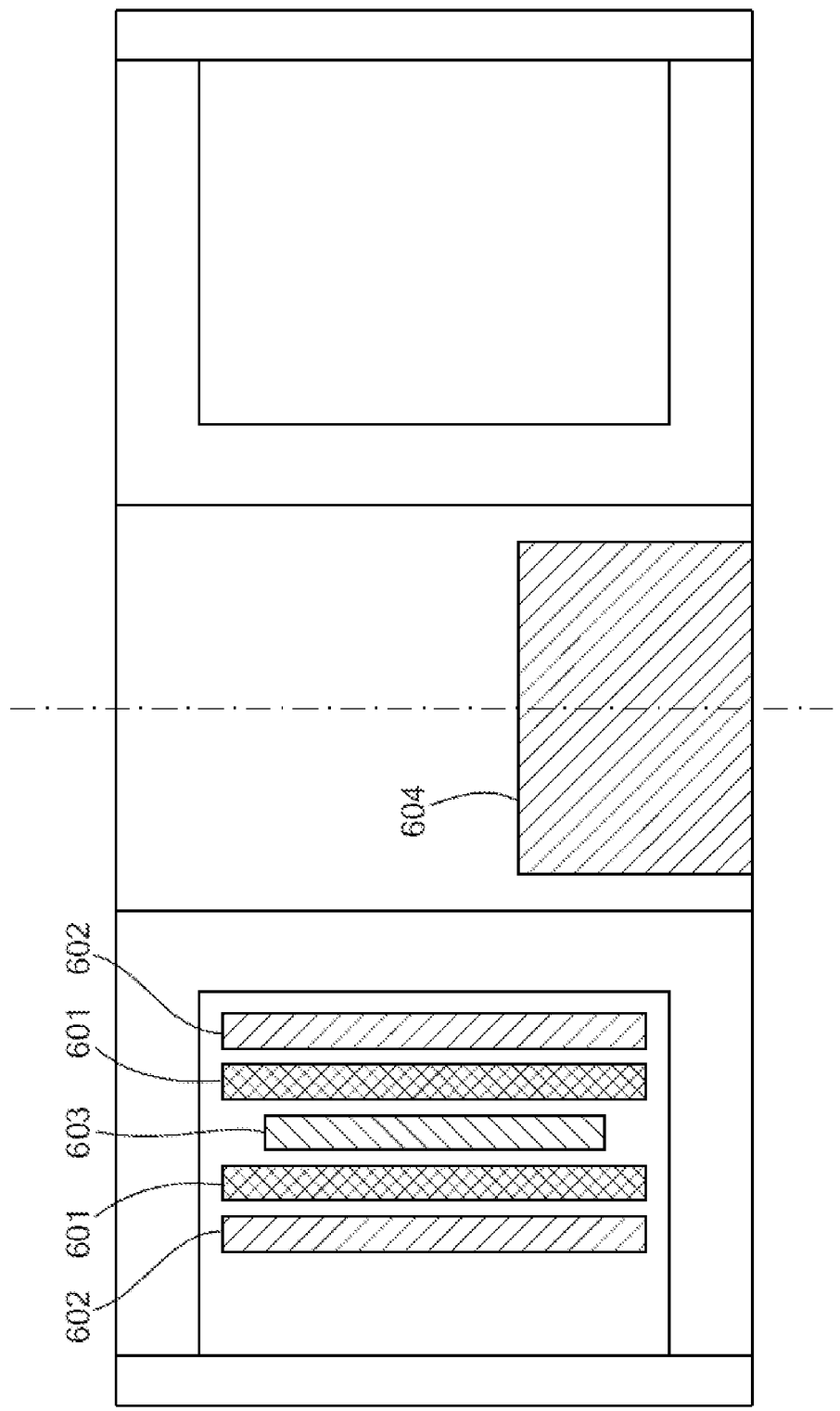

EXTERNAL BUTTON PROCESSOR WITH A RECHARGEABLE BATTERY

This application is a continuation of U.S. patent application Ser. No. 13/632,182, filed Oct. 1, 2012, which is a continuation of U.S. patent application Ser. No. 12/534,298, filed Aug. 3, 2009, which claims priority from U.S. Provisional Patent Application 61/087,276, filed Aug. 8, 2008. These applications are incorporated herein by reference in their respective entireties.

FIELD OF THE INVENTION

The invention generally relates to implantable prosthetic systems such as cochlear implants, and specifically to the external structures of such systems.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

Existing cochlear implant systems need to deliver electrical power from outside the body through the skin to satisfy the power requirements of the implanted portion of the system. FIG. 1 shows a typical arrangement based on inductive coupling through the skin to transfer both the required electrical power and the processed audio information. As shown in FIG. 1, an external transmitter coil 107 (coupled to the external signal processor) is placed on the skin adjacent to a subcutaneous receiver coil in the implant 108. Often, a magnet in the external coil structure interacts with a corresponding magnet in the subcutaneous secondary coil structure. This arrangement inductively couples a radio frequency (rf) electrical signal to the receiver in the implant 108, which is able to extract from the rf signal both the audio information for the implanted portion of the system and a power component to power the implanted system.

In most prior systems, the external components generally have been held in separate housings so that the external transmitter coil 107 would not be in the same physical housing as the power source or the external signal processor. The various different physical components would generally be connected by hard wire, although some systems used wireless links between separate external components. A few systems have been proposed in which all of the external components such as an external processor and a rechargeable battery could be placed within a single housing. See U.S. Patent Publication 20080002834 (Hochmair) and U.S. Patent Publication 20070053534 (Kiratzidis), which are incorporated herein by reference.

The rechargeable batteries (e.g. Lithium-Ion batteries) for such systems have conductive band materials such as aluminum and copper which are coated with battery chemistry (e.g. graphite) and are stacked on top of each other. But when such a battery is placed within a magnetic field generated by a current-carrying coil, the conductive band materials generate undesired eddy currents. Excessive eddy currents are a significant problem because they cause decreased coupling which reduces efficiency.

U.S. Pat. No. 6,067,474 by Schulman et al. teaches a coil design in the form of a long ribbon of battery electrodes. Conductive band materials are wound in a spiral (see FIGS. 7 and 9) so that the magnetic field lines generated by a coil are parallel to the conductive band materials thereby reducing eddy currents. One drawback of this approach is that in the region of overlapping conductive band materials, adjacent cathodic (46') and anodic (48') bands (separated by an insulator material (50', 52')) act as parallel plate capacitors. Such capacitance in turn may seriously increase the impedance of the coil and thereby reduce the efficiency of data and power transmission between the external coil and the implanted coil.

SUMMARY OF THE INVENTION

Embodiments of the invention are directed to an external processor device for a hearing implant system. An external processor housing has a generally planar skin contacting surface and a central axis perpendicular to the skin contacting surface. A signal processor is located within the processor housing for developing an implant data signal. The processor housing also contains a transmitter coil for coupling the implant data signal across the skin to the implantable prosthetic system. A battery container forms an annular compartment around the central axis and contains a battery arrangement to provide electrical power to the signal processor and the transmitter coil. An external positioning magnet is radially inward of the battery container for magnetically interacting with a corresponding internal positioning magnet in the implantable prosthetic system to hold the external processor device in a fixed position on the skin.

The battery container may form a complete annular ring or a partial annular ring around the central axis. The battery arrangement may use one or more rechargeable batteries and/or replaceable batteries. The battery arrangement may also include multiple battery cells, each of which occupies a partial annular section within the battery container. In such an embodiment, each battery cell may have the same size, or one of the battery cells may be larger than the others. The external processor device may further have a center of mass displaced from the central axis so as to define a preferred rotational position of the external processor device on the skin with the center of mass below the central axis.

The hearing implant system may be a cochlear implant system. Embodiments of the invention also include a replacement battery arrangement for a device according to any of the above. Embodiments also include an implantable device having such a battery arrangement.

BRIEF DESCRIPTION OF THE DRAWINGS

FIG. 6 shows the arrangement of multiple battery plates in a battery cell.

DETAILED DESCRIPTION OF SPECIFIC EMBODIMENTS

Embodiments of the present invention are directed to a novel battery arrangement for an external processor housing of a hearing implant system that reduces the influence of eddy currents in inductively coupled coils. The capacitive effects of the battery arrangement are minimized and a rotational position is defined for the processor housing.

Figure 1:
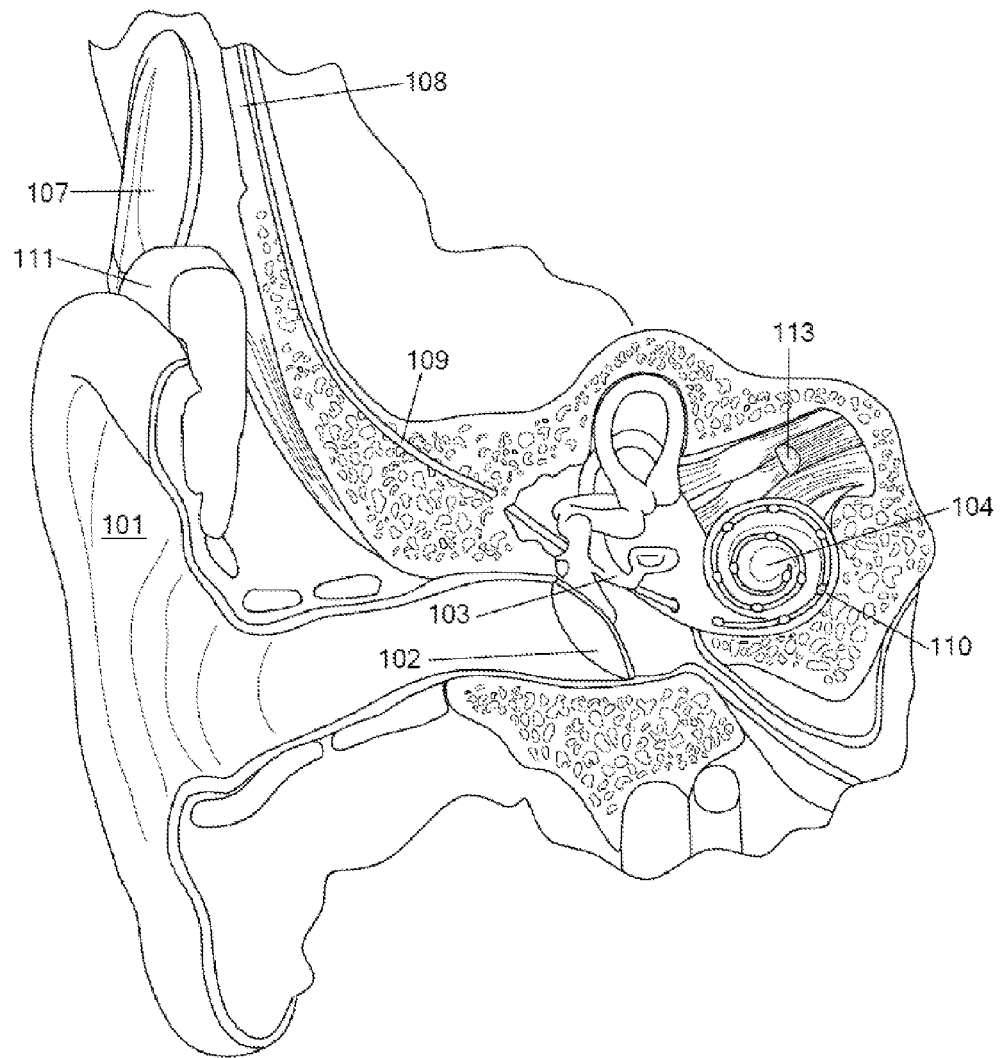
FIG. 1 shows a human auditory system with a cochlear implant.
Figure 2:
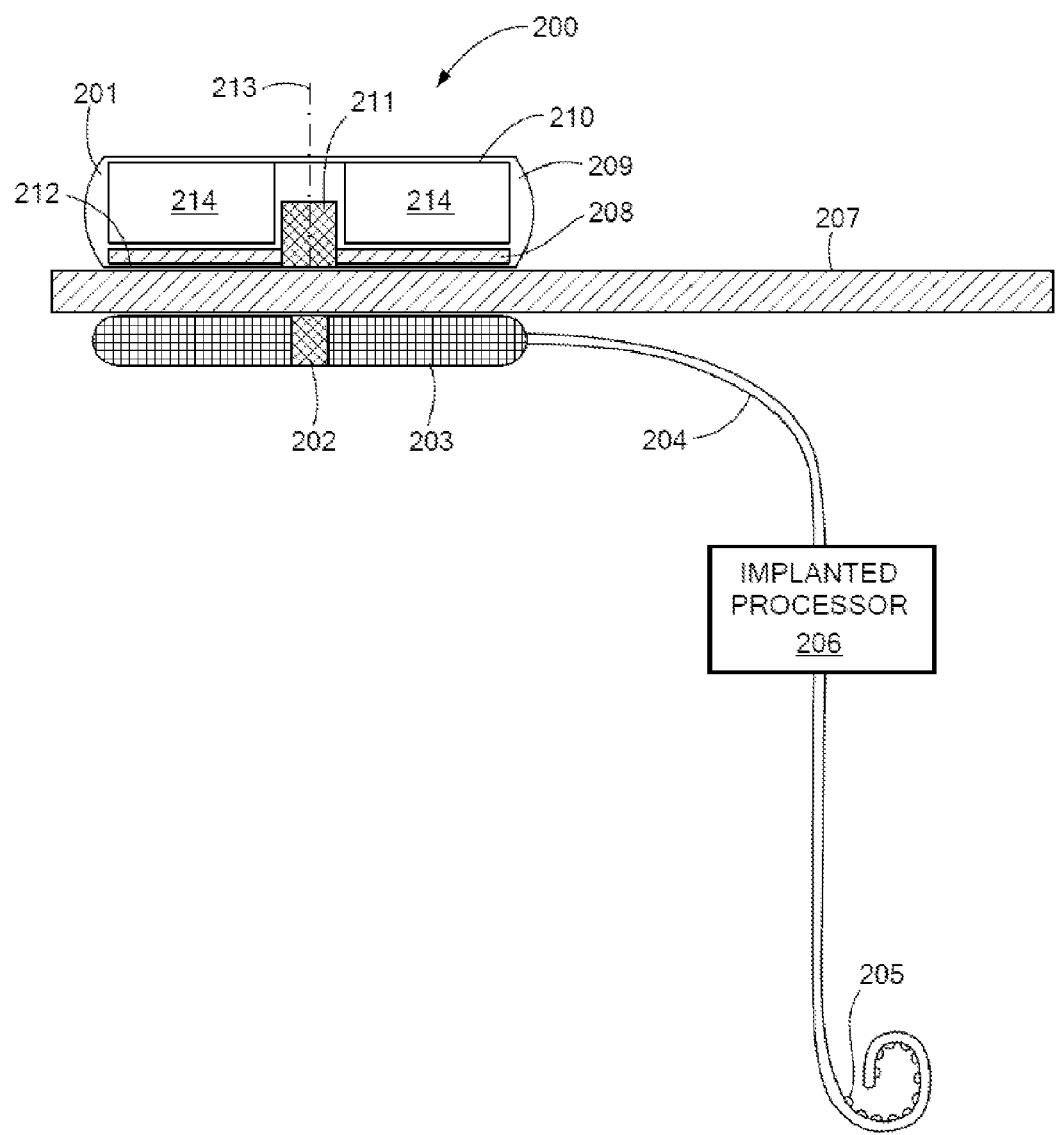
FIG. 2 shows various elements in a system having an external device according to one embodiment of the present invention.

FIG. 2 shows elements of an embodiment in which an external processor housing 200 has a generally planar skin contacting surface 212 and a central axis 213 that is perpendicular to the skin contacting surface. A signal processor 209 is located within the processor housing 200 for developing an implant data signal. The processor housing 200 also contains a transmitter coil 208 for coupling the implant data signal across the skin 207. A rechargeable battery arrangement 214 is contained within a battery compartment 210 which is located in an annular region around the central axis 213. The battery compartment 210 may form a complete annular ring around the central axis 213, or a partial annular section about the central axis 213.

The battery arrangement 214 provides electrical power to the signal processor 209 and the transmitter coil 208. An external positioning magnet 211 is located radially inward of the battery compartment 210 and magnetically interacts with a corresponding internal positioning magnet 202 to hold the external transmitter coil 208 in a fixed position on the skin 207 over an implant coil 203 having its own implant holding magnet 202. By this arrangement, the implant data signal is coupled by the transmitter coil 208 across the skin 207 to the implant coil 203. The implant coil 203 is connected by implanted wires 204 to an implant processor 206 which develops a stimulation signal for the implanted electrode array 205 which stimulates audio nerve tissue in the cochlea.

Figure 4:
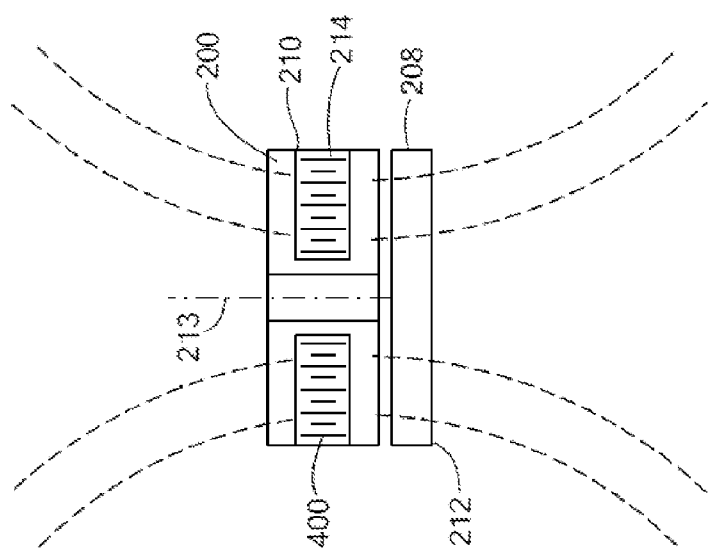
FIG. 4 shows a side view as in FIG. 3 with the addition of a processor housing according to one embodiment.
Figure 3:
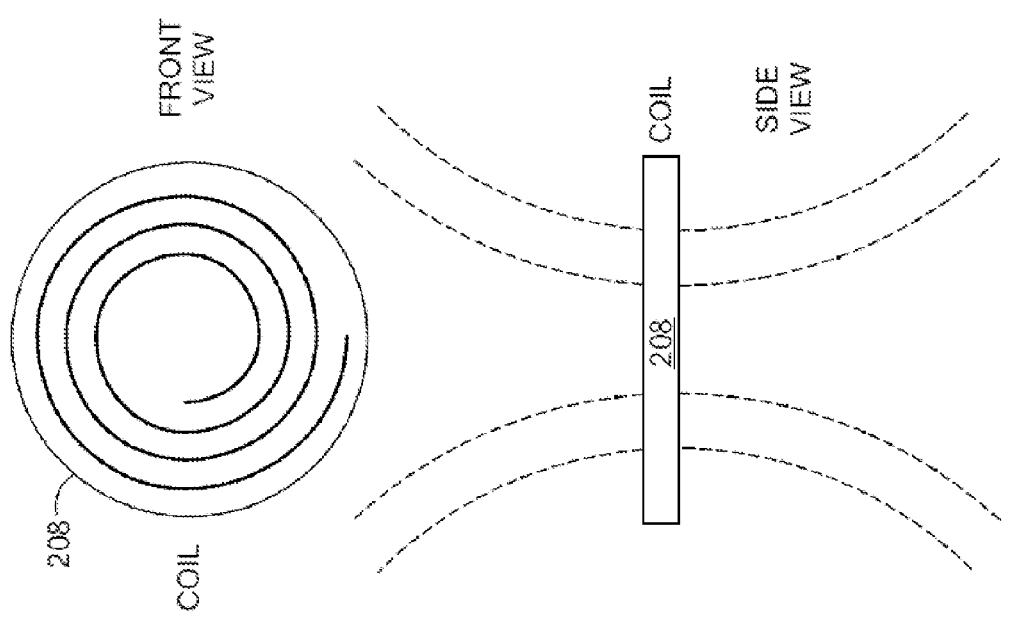
FIG. 3 shows front and side views of the transmitter coil and the resulting lines of magnetic force.
Figure 5:
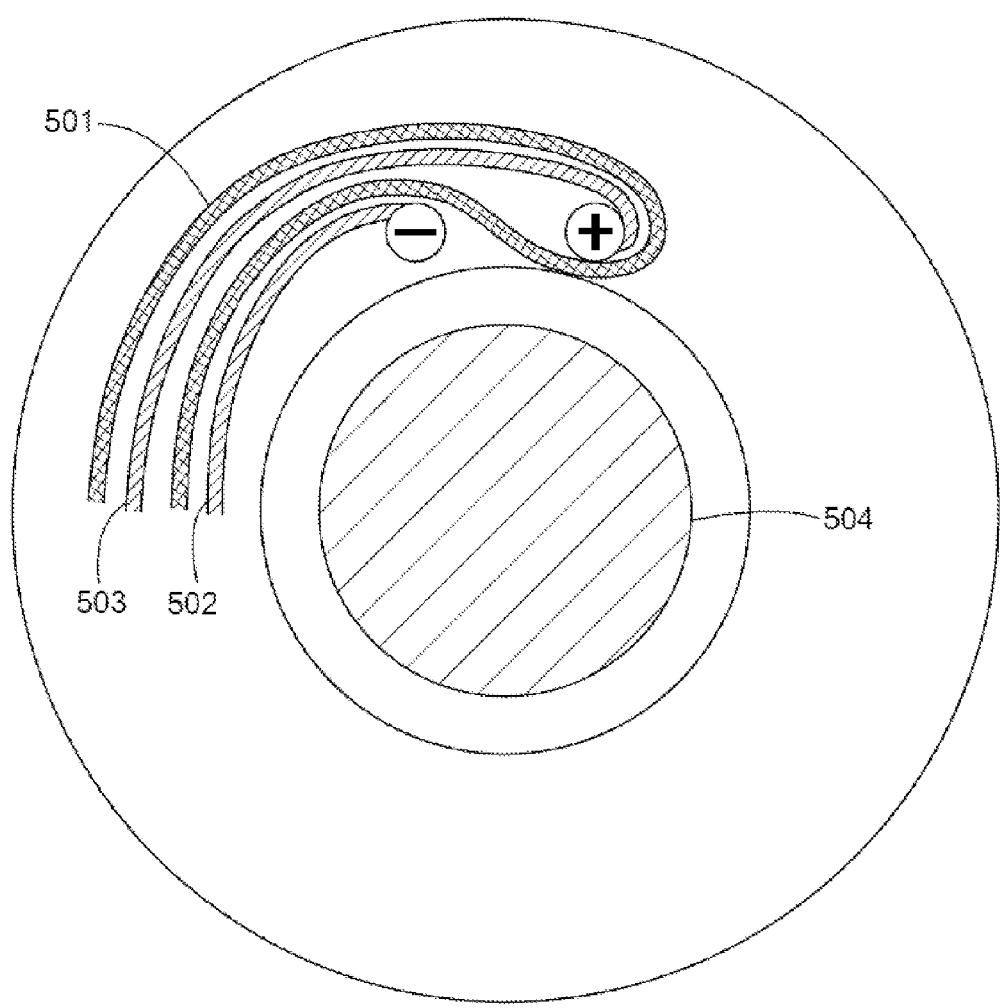
FIG. 5 shows detail regarding the arrangement of conductive band materials in a battery cell according to one embodiment.

FIG. 3 shows front and side views of the transmitter coil 208 along with a depiction of the lines of the magnetic field produced by the coil when transmitting the implant data signal. FIG. 4 shows a side view of the same thing with the addition of the battery compartment 210 and showing that the battery arrangement 214 includes multiple conductive band plates 400 arranged to be parallel to the magnetic field lines that originate from the transmitter coil 208. FIG. 5 provides further detail of the arrangement of the conductive plates showing a cathode band 503 and an anode band 502 which are separated by a u-shaped non-conductive separator band 501. As shown in FIG. 6, an actual battery cell would have multiple such bands forming multiple anode plates 602 and cathode plates 603 separated by multiple non-conductive separator plates 601.

Figure 7A:
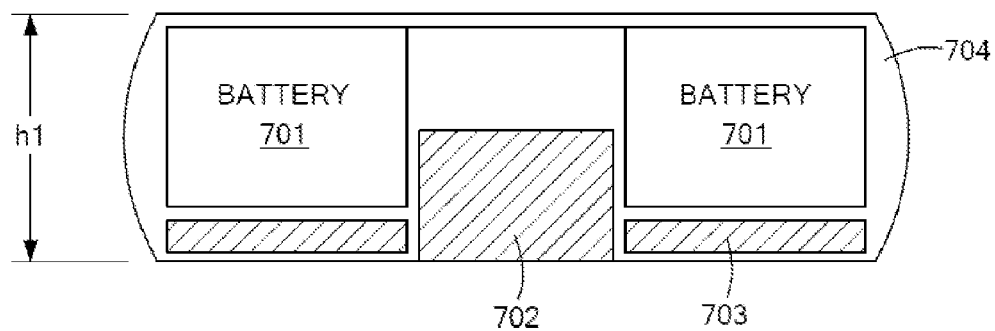
FIGS. 7A-7B show the reduced height of the processor housing due to the improved arrangement of the battery.
Figure 7B:
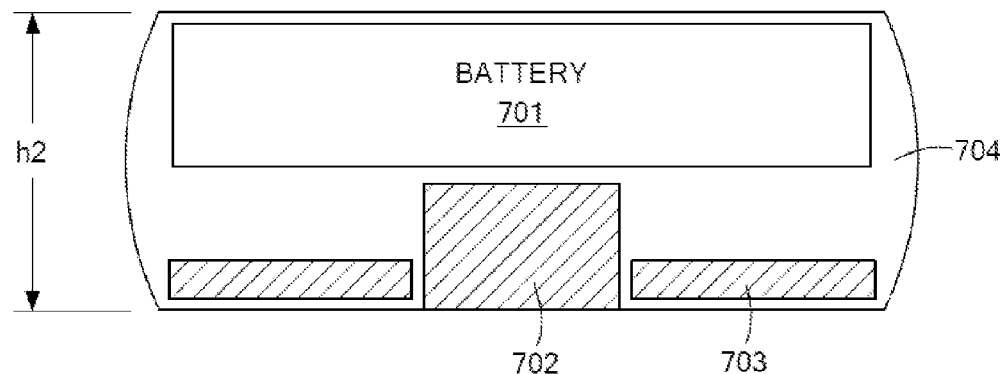

FIG. 7 shows how such an annular battery arrangement enables a lower height profile for the external processor housing. The height h1 of an external processor housing according to an embodiment of the present invention as in FIG. 7A is significantly less than the height h2 of a prior art external processor housing as shown in FIG. 7B. Although the relative structures of the external holding magnet 702 and transmitter coils 703 is the same in both, in the prior art arrangement as shown in FIG. 7B, the battery 701 fits over the holding magnet 702, whereas in an embodiment of the present invention as shown in FIG. 7A, the battery 701 does not fit over the holding magnet 702 but instead occupies an annular region radially outward of the magnet.

Figure 8:
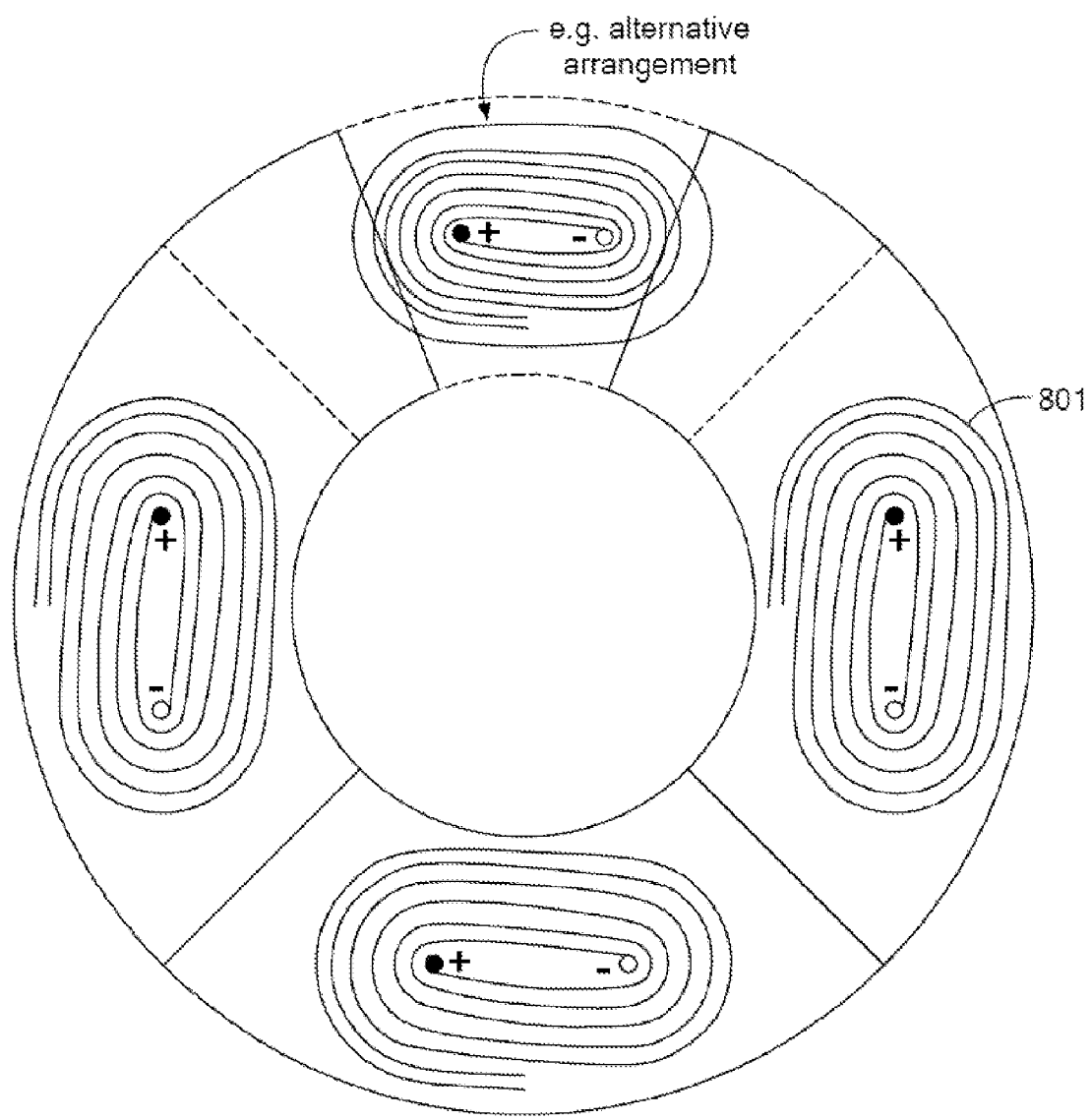
FIG. 8 shows the arrangement of multiple battery cells in annular sections around the central axis.
Figure 9:
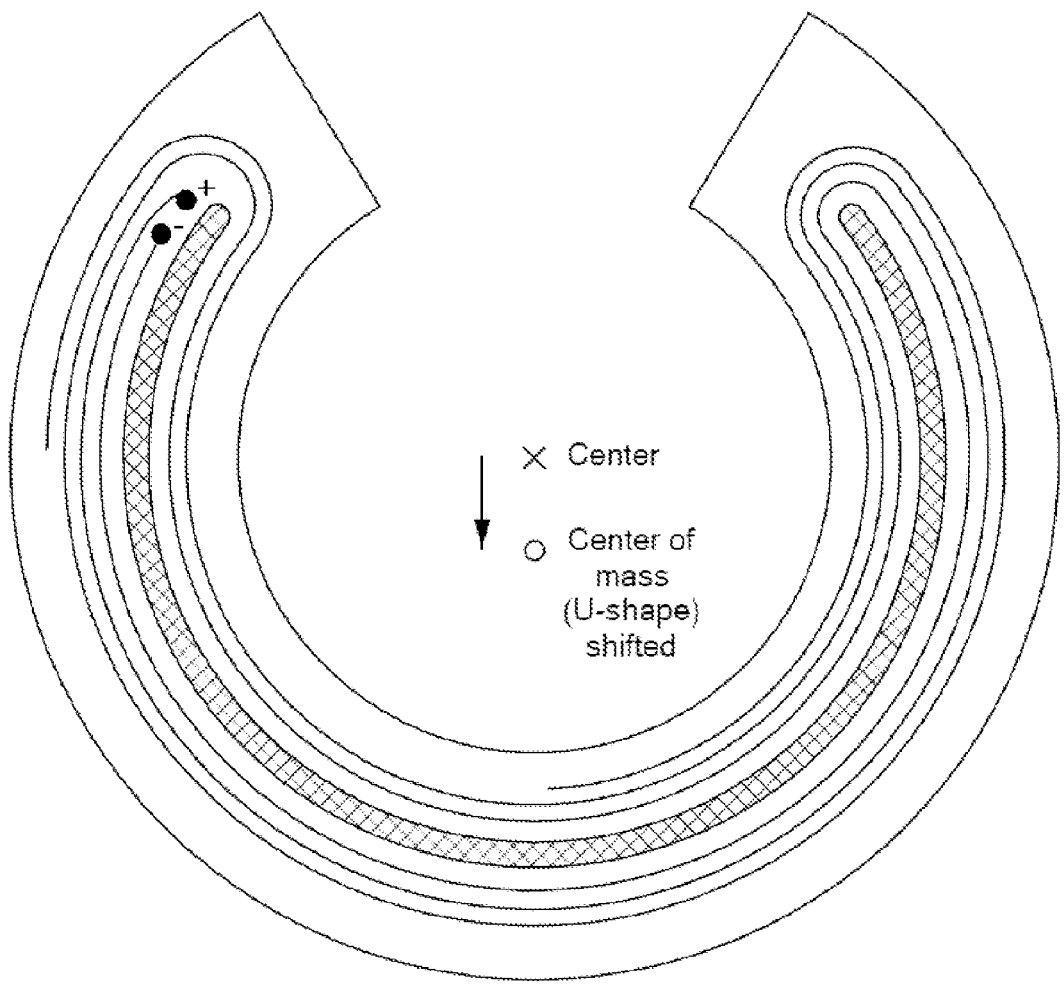
FIG. 9 shows how embodiments of the present invention displace the center of mass away from the central axis to define a preferred rotational position.

As shown in FIG. 8, the battery arrangement may include multiple battery cells 801, each of which occupies an annular section within the battery compartment. Such arrangements reduce capacitive effects in regions of overlapping conductive cathodic and anodic band materials, which in turn minimizes undesired eddy currents and leads to greater efficiency. In such an embodiment, each battery cell 801 may have the same size, or in some embodiments, one of the battery cells 801 may be larger than the others thereby defining a preferred rotational position due to the resulting shift in the center of mass away from the central axis. As shown in FIG. 9, the external processor device may have a battery compartment that forms a u-shaped annular region extending more than halfway around the central axis so that the center of mass is displaced from the central axis so as to define a preferred rotational position of the device on the skin with the center of mass below the central axis. Alternatively the holding magnet or some other relatively heavy component could be offset from the central axis to define a preferred rotational position.

Figure 10:
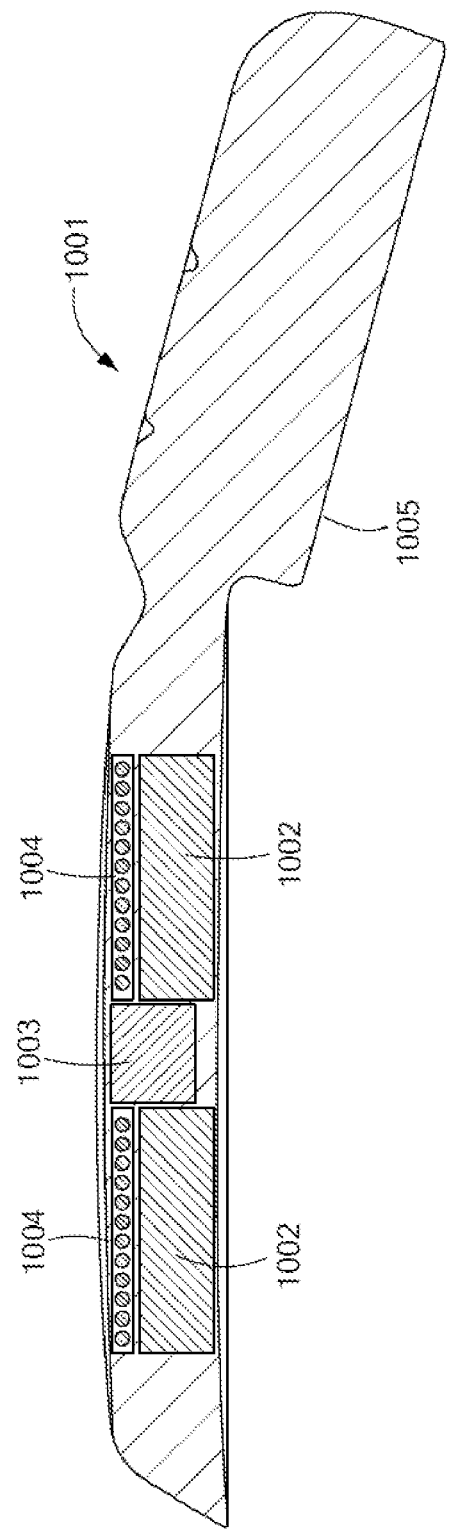
FIG. 10 shows an example of an implantable device having a battery arrangement according to an embodiment of the present invention.

As shown in FIG. 10, the same principles can be used in an implant having receiving coils and a rechargeable battery. FIG. 10 shows an implantable housing 1001 for a cochlear implant system having a stimulator module 1005 that develops the received implant data signal into one or more electrical stimulation signals for application to audio nerve tissue, e.g., in the cochlear of the patient. An implant holding magnet 1003 is surrounded by implant coils 1004 and the rechargeable implant battery 1002 overlays the implant coils 1004 in an annular region around the implant holding magnet 1003.

As with the external housing arrangements discussed above, the implant battery 1002 may be arranged in one or more battery cells in a complete annular ring, or in a partial annular section.

Although various exemplary embodiments of the invention have been disclosed, it should be apparent to those skilled in the art that various changes and modifications can be made which will achieve some of the advantages of the invention without departing from the true scope of the invention. For example, embodiments of the invention also include a replacement battery arrangement for a device according to any of the above.

What is claimed is:

1. An external processor device, for a hearing implant system that stimulates audio nerve tissue in a cochlea based on an implant data signal, the device comprising:

an external processor housing having a generally planar skin contacting surface and a central axis perpendicular to the skin contacting surface;

a signal processor within the processor housing for developing the implant data signal;

a transmitter coil within the processor housing for coupling the implant data signal across the skin to the hearing implant system; and a battery container forming an annular compartment around the central axis and containing a battery arrangement to provide electrical power to the signal processor and the transmitter coil;

wherein the battery arrangement includes a plurality of battery cells, each battery cell occupying a respective annular section within the battery container, the respective annular sections being arranged in the battery arrangement so as to minimize an eddy current produced in a coil, of the hearing implant system, that is inductively coupled to the transmitter coil.

2. A device according to claim 1, further comprising:

an external positioning magnet radially inward of the battery container for magnetically interacting with a corresponding internal positioning magnet in the implantable prosthetic system to hold the device in a fixed position on the skin.

3. A device according to claim 1, wherein the battery container forms a complete annular ring around the central axis.

4. A device according to claim 1, wherein the battery container forms a partial annular ring around the central axis.

5. A device according to claim 1, wherein each battery cell has the same size.

6. A device according to claim 1, wherein one of the battery cells is larger than the others.

7. A device according to claim 1, wherein the external processor device has a center of mass displaced from the central axis so as to define a preferred rotational position of the external processor device on the skin with the center of mass below the central axis.

8. A device according to claim 1, wherein the battery arrangement uses one or more rechargeable batteries.

9. A device according to claim 1, wherein the battery arrangement uses one or more replaceable batteries.

* * * * *